United States Patent
Dempsey et al.

(10) Patent No.: US 10,034,829 B2
(45) Date of Patent: Jul. 31, 2018

(54) SEMI-PERMANENT MASCARA COMPOSITIONS

(75) Inventors: James Herman Dempsey, Danbury, CT (US); Thomas Elliot Rabe, Baltimore, MD (US)

(73) Assignee: Noxell Corporation, Hunt Valley, MD (US)

( * ) Notice: Subject to any disclaimer, the term of this patent is extended or adjusted under 35 U.S.C. 154(b) by 18 days.

(21) Appl. No.: 13/274,852

(22) Filed: Oct. 17, 2011

(65) Prior Publication Data

US 2012/0114585 A1 May 10, 2012

Related U.S. Application Data

(60) Provisional application No. 61/455,843, filed on Oct. 27, 2010.

(51) Int. Cl.
*A61K 8/92* (2006.01)
*A61K 8/26* (2006.01)
*A61K 8/37* (2006.01)
*A61Q 1/10* (2006.01)

(52) U.S. Cl.
CPC .............. *A61K 8/922* (2013.01); *A61K 8/26* (2013.01); *A61K 8/37* (2013.01); *A61Q 1/10* (2013.01)

(58) Field of Classification Search
CPC ....................................................... A61K 8/26
See application file for complete search history.

(56) References Cited

U.S. PATENT DOCUMENTS

| | | | |
|---|---|---|---|
| 2,458,063 A | 1/1949 | Duhiberg |
| 2,831,854 A | 4/1958 | Tucker |
| 2,900,306 A | 8/1959 | Slater |
| 3,255,082 A | 6/1966 | Barton |
| 3,677,271 A | 7/1972 | Luciano |
| 3,690,777 A | 9/1972 | Costa |
| 3,739,789 A | 6/1973 | Cataneo |
| 3,802,841 A | 4/1974 | Robin |
| 3,963,699 A | 6/1976 | Rizzi et al. |
| 4,005,195 A | 1/1977 | Jandacek |
| 4,005,196 A | 1/1977 | Jandacek et al. |
| 4,126,679 A | 11/1978 | Davy et al. |
| 4,137,306 A | 1/1979 | Rubino et al. |
| 4,151,272 A | 4/1979 | Geary et al. |
| 4,154,816 A | 5/1979 | Roehl et al. |
| D252,911 S | 9/1979 | Levy |
| 4,202,879 A | 5/1980 | Shelton |
| 4,226,889 A | 10/1980 | Yuhas |
| 4,228,277 A | 10/1980 | Landoll |
| 4,229,432 A | 10/1980 | Geria |
| 4,280,994 A | 7/1981 | Turney |
| 4,322,400 A | 3/1982 | Yuhas |
| 4,336,246 A | 6/1982 | Leon-Pekarek |
| 4,346,079 A | 8/1982 | Roehl |
| D267,822 S | 2/1983 | Katz et al. |
| 4,383,988 A | 5/1983 | Teng et al. |
| D277,324 S | 1/1985 | Davey |
| 4,517,360 A | 5/1985 | Volpenhein |
| 4,518,772 A | 5/1985 | Volpenhein |
| 4,725,432 A | 2/1988 | May |
| 4,759,924 A | 7/1988 | Luebbe et al. |
| 4,781,917 A | 11/1988 | Luebbe et al. |
| 4,797,300 A | 1/1989 | Jandacek et al. |
| 4,816,261 A | 3/1989 | Luebbe et al. |
| 4,886,080 A | 12/1989 | Cole |
| 4,932,802 A | 6/1990 | Cantone |
| 4,980,155 A | 12/1990 | Shah |
| 4,993,858 A | 2/1991 | Mock |
| 5,017,398 A | 5/1991 | Jandacek et al. |
| 5,019,375 A | 5/1991 | Tanner et al. |
| 5,040,914 A | 8/1991 | Fitjer |
| 5,056,179 A | 10/1991 | Capponi |
| 5,097,853 A | 3/1992 | Nehashi |
| 5,104,646 A | 4/1992 | Bolich, Jr. et al. |
| RE33,996 E | 7/1992 | Jandacek |
| 5,165,917 A | 11/1992 | Zabotto |
| 5,193,918 A | 3/1993 | Lohrmann et al. |
| 5,217,641 A | 6/1993 | Herstein |
| 5,306,514 A | 4/1994 | Letton et al. |
| 5,306,515 A | 4/1994 | Letton et al. |
| 5,306,516 A | 4/1994 | Letton et al. |
| RE34,617 E | 5/1994 | Jandacek et al. |
| D348,123 S | 6/1994 | Wu |
| 5,376,231 A | 12/1994 | Matsumoto et al. |
| 5,389,363 A | 2/1995 | Snyder |
| D360,486 S | 7/1995 | Schultz |
| 5,490,529 A | 2/1996 | Fitjer |
| 5,509,742 A | 4/1996 | Balzarini |
| D370,088 S | 5/1996 | Burns |
| 5,794,632 A | 8/1998 | Gueret |
| 5,832,942 A | 11/1998 | Gutberlet |

(Continued)

FOREIGN PATENT DOCUMENTS

| CA | 2773443 A1 | 5/2011 |
| CA | 2773578 A1 | 5/2011 |

(Continued)

OTHER PUBLICATIONS

U.S. Appl. No. 61/487,149, filed May 17, 2011, Haimi Bekele, et al.

(Continued)

*Primary Examiner* — Hasan Ahmed (74) *Attorney, Agent, or Firm* — Schwegman, Lundberg & Woessner, P.A.

(57) ABSTRACT

A semi-permanent mascara composition for use on eyelashes and/or eyelids that includes from 17% to 30%, by weight, of a film former selected from the group consisting of tall oil glyceride, pentaerythrityl rosinate, glyceryl rosinate, and the hydrogenated versions and mixtures thereof. Further there is from 0.1% to 14%, by weight, of a colorant and from 10% to 15%, by weight, of disteardimonium hectorite, and less than about 3% of wax. The semi-permanent mascara composition is long lasting and has excellent wear characteristics.

51 Claims, 5 Drawing Sheets

(56) References Cited

U.S. PATENT DOCUMENTS

| | | |
|---|---|---|
| 5,843,417 A | 12/1998 | Hanna et al. |
| 5,866,434 A | 2/1999 | Massey et al. |
| 5,874,072 A | 2/1999 | Alwattari et al. |
| 5,996,780 A | 12/1999 | Gurrera |
| D419,266 S | 1/2000 | Gobe |
| D422,748 S | 4/2000 | Lang |
| 6,071,503 A | 6/2000 | Drechsler et al. |
| 6,074,654 A | 6/2000 | Drechsler et al. |
| 6,080,687 A | 6/2000 | Ishwarlal |
| 6,139,823 A | 10/2000 | Drechsler et al. |
| 6,200,045 B1 | 3/2001 | Hahn et al. |
| 6,203,814 B1 | 3/2001 | Fisher et al. |
| 6,241,408 B1 | 6/2001 | Lang |
| 6,267,951 B1 | 7/2001 | Shah |
| 6,303,105 B1 | 10/2001 | Shah et al. |
| D450,888 S | 11/2001 | Breidenbach et al. |
| 6,340,466 B1 | 1/2002 | Drechsler et al. |
| D453,588 S | 2/2002 | Breidenbach et al. |
| D453,589 S | 2/2002 | Breidenbach et al. |
| 6,450,179 B2 | 9/2002 | Bengis |
| 6,464,418 B1 | 10/2002 | Visser |
| 6,488,427 B1 | 12/2002 | Breidenbach et al. |
| 6,491,902 B2 | 12/2002 | Shefer et al. |
| 6,500,446 B1 | 12/2002 | Derrieu et al. |
| D474,341 S | 5/2003 | Cantone et al. |
| 6,612,764 B2 | 9/2003 | Dumler |
| 6,637,963 B2 | 10/2003 | Huang |
| D482,284 S | 11/2003 | Cantone et al. |
| 6,682,242 B1 | 1/2004 | Montoli |
| D491,810 S | 6/2004 | Kostow |
| D491,811 S | 6/2004 | Kostow |
| D497,455 S | 10/2004 | Lee |
| 6,811,770 B2 | 11/2004 | Ferrari |
| 6,827,516 B2 | 12/2004 | Gutberlet |
| 6,896,433 B1 | 5/2005 | Zhang |
| 6,979,440 B2 | 12/2005 | Shefer et al. |
| 6,985,879 B2 | 1/2006 | Walker et al. |
| 7,077,591 B2 | 7/2006 | Gueret |
| D530,857 S | 10/2006 | Black |
| 7,168,875 B1 | 1/2007 | Zhang |
| 7,175,359 B2 | 2/2007 | Zhang |
| 7,186,274 B2 | 3/2007 | Vic et al. |
| D542,978 S | 5/2007 | Bortolotti |
| 7,210,870 B2 | 5/2007 | Breidenbach et al. |
| 7,226,227 B2 | 6/2007 | Gueret |
| 7,241,835 B2 | 7/2007 | O'Brien et al. |
| 7,276,088 B2 | 10/2007 | Huang et al. |
| D561,390 S | 2/2008 | Sugawara |
| D566,335 S | 4/2008 | Althoff et al. |
| D566,337 S | 4/2008 | Althoff et al. |
| D574,154 S | 8/2008 | Dumler et al. |
| D574,155 S | 8/2008 | Dumler et al. |
| D578,770 S | 10/2008 | Berhault |
| D579,208 S | 10/2008 | Berhault |
| 7,438,953 B2 | 10/2008 | Kotov et al. |
| D581,169 S | 11/2008 | Berhault |
| D583,506 S | 12/2008 | Justice |
| D585,600 S | 1/2009 | Althoff et al. |
| 7,473,045 B2 | 1/2009 | Dumler |
| D592,858 S | 5/2009 | Berhault |
| D593,330 S | 6/2009 | Berhault |
| D593,331 S | 6/2009 | Berhault |
| D598,657 S | 8/2009 | Berhault |
| D600,921 S | 9/2009 | Berhault |
| D600,922 S | 9/2009 | Berhault |
| D600,923 S | 9/2009 | Berhault |
| 7,632,489 B2 | 12/2009 | Wyatt et al. |
| D615,419 S | 5/2010 | Owen |
| 7,780,875 B2 | 8/2010 | Asgari |
| 7,842,285 B2 | 11/2010 | Lu et al. |
| 7,856,806 B1 | 12/2010 | Chasman |
| D634,127 S | 3/2011 | Burgess et al. |
| D634,478 S | 3/2011 | Kolas et al. |
| D636,940 S | 4/2011 | Acierto |
| D642,805 S | 8/2011 | Burgess |
| 7,993,661 B2 | 8/2011 | Arnaud et al. |
| D653,398 S | 1/2012 | Acierto et al. |
| 8,096,306 B2 | 1/2012 | Malvar et al. |
| D654,626 S | 2/2012 | Kolas et al. |
| 8,168,095 B2 | 5/2012 | Alberius et al. |
| 8,298,494 B2 | 10/2012 | Komiya et al. |
| 8,323,628 B2 | 12/2012 | Atis |
| 8,329,147 B2 | 12/2012 | Ansmann et al. |
| 8,335,560 B2 | 12/2012 | Wei |
| 8,336,560 B2 | 12/2012 | Dumler et al. |
| 8,444,930 B2 | 5/2013 | Komiya et al. |
| 9,216,145 B2 | 12/2015 | Rabe et al. |
| 9,237,992 B2 | 1/2016 | Hodgetts et al. |
| 2001/0051168 A1 | 12/2001 | Ramin et al. |
| 2002/0071707 A1 | 6/2002 | Breidenbach |
| 2002/0076390 A1 | 6/2002 | Kantner et al. |
| 2002/0083954 A1 | 7/2002 | Gavney |
| 2002/0185148 A1 | 12/2002 | Bengis |
| 2002/0190336 A1 | 12/2002 | Shimizu et al. |
| 2003/0031642 A1 | 2/2003 | Lezer |
| 2003/0041870 A1 | 3/2003 | Su |
| 2003/0086741 A1 | 5/2003 | Kim |
| 2003/0095935 A1 | 5/2003 | Chaiyawat et al. |
| 2003/0143181 A1 | 7/2003 | Hensen et al. |
| 2004/0105828 A1 | 6/2004 | Chaiyawat et al. |
| 2004/0115232 A1 | 6/2004 | Giroud et al. |
| 2004/0126303 A1 | 7/2004 | Hwang |
| 2004/0142831 A1 | 7/2004 | Lezer |
| 2004/0190974 A1 | 9/2004 | Cantone et al. |
| 2004/0228890 A1 | 11/2004 | Blin |
| 2004/0234564 A1 | 11/2004 | Blin |
| 2005/0061349 A1 | 3/2005 | Patel et al. |
| 2005/0095213 A1 | 5/2005 | Blin |
| 2005/0176598 A1 | 8/2005 | Bergquist et al. |
| 2005/0186167 A1 | 8/2005 | Ueda et al. |
| 2005/0276779 A1 | 12/2005 | Blin |
| 2006/0029560 A1 | 2/2006 | Blin |
| 2006/0067783 A1 | 3/2006 | Tsaur |
| 2006/0084586 A1 | 4/2006 | Drzewinski et al. |
| 2006/0127339 A1 | 6/2006 | Bavouzet |
| 2006/0134035 A1 | 6/2006 | Zheng et al. |
| 2006/0189554 A1 | 8/2006 | Mumper et al. |
| 2006/0260633 A1 | 11/2006 | Wyatt et al. |
| 2006/0275232 A1 | 12/2006 | Chevalier |
| 2006/0275235 A1 | 12/2006 | Takeda et al. |
| 2007/0014745 A1 | 1/2007 | Arnaud |
| 2007/0020205 A1 | 1/2007 | Blin |
| 2007/0041920 A1 | 2/2007 | Blin |
| 2007/0048238 A1* | 3/2007 | Sandewicz et al. ............ 424/63 |
| 2007/0140991 A1 | 6/2007 | Maitra et al. |
| 2007/0274941 A9 | 11/2007 | Blin |
| 2007/0286824 A1 | 12/2007 | Rabe et al. |
| 2008/0000491 A1 | 1/2008 | Bodelin |
| 2008/0014232 A1 | 1/2008 | Arnaud |
| 2008/0031834 A1 | 2/2008 | Manelski et al. |
| 2008/0056807 A1 | 3/2008 | Vintimiglia |
| 2008/0107615 A1* | 5/2008 | Keene et al. ................ 424/70.7 |
| 2008/0115798 A1 | 5/2008 | Rainey et al. |
| 2008/0124350 A1 | 5/2008 | Mumper et al. |
| 2008/0171009 A1 | 7/2008 | Auguste |
| 2008/0226575 A1 | 9/2008 | Hanna |
| 2008/0311063 A1 | 12/2008 | Shah |
| 2009/0010868 A1 | 1/2009 | Ilekti |
| 2009/0098170 A1 | 4/2009 | D'Acchioli et al. |
| 2009/0142282 A1 | 6/2009 | Kendall |
| 2009/0193602 A1 | 8/2009 | Dumler |
| 2009/0193692 A1 | 8/2009 | Lipczynski |
| 2009/0263658 A1 | 10/2009 | Alberius et al. |
| 2009/0271932 A1 | 11/2009 | Alberius et al. |
| 2009/0317350 A1 | 12/2009 | Lu |
| 2010/0003205 A1 | 1/2010 | Elliott et al. |
| 2010/0003293 A1 | 1/2010 | Elliott et al. |
| 2010/0028612 A1 | 2/2010 | Gruber et al. |
| 2010/0068163 A1 | 3/2010 | Lu |
| 2010/0074928 A1 | 3/2010 | Elliott et al. |
| 2010/0152135 A1 | 6/2010 | Blin |
| 2010/0179105 A1 | 7/2010 | Blin |
| 2011/0014249 A1 | 1/2011 | Mateu et al. |
| 2011/0094533 A1 | 4/2011 | Dempsey |

(56) References Cited

U.S. PATENT DOCUMENTS

| | | |
|---|---|---|
| 2011/0094914 A1 | 4/2011 | Dempsey |
| 2011/0117040 A1 | 5/2011 | Dempsey |
| 2011/0117043 A1 | 5/2011 | Dempsey |
| 2011/0142781 A1 | 6/2011 | Kaftan et al. |
| 2011/0268490 A1 | 11/2011 | Acierto et al. |
| 2012/0114585 A1 | 5/2012 | Dempsey et al. |
| 2012/0269753 A1 | 10/2012 | Rabe et al. |
| 2012/0298128 A1 | 11/2012 | Hodgetts et al. |
| 2012/0315076 A1 | 12/2012 | Bekele et al. |
| 2013/0012594 A1 | 1/2013 | Hirasawa et al. |
| 2013/0056016 A1 | 3/2013 | Guay et al. |
| 2013/0056019 A1 | 3/2013 | Wilson et al. |
| 2013/0056020 A1 | 3/2013 | Wilson et al. |
| 2014/0308230 A1 | 10/2014 | Metten |
| 2017/0065513 A1 | 3/2017 | Zhu et al. |

FOREIGN PATENT DOCUMENTS

| | | |
|---|---|---|
| CN | 1636538 A | 7/2005 |
| CN | 101272823 A | 9/2008 |
| CN | 300856708 | 12/2008 |
| CN | 300856709 | 12/2008 |
| CN | 300856710 | 12/2008 |
| CN | 102360418 A | 2/2012 |
| CN | 104245048 A | 12/2014 |
| DE | 3923731 A | 1/1991 |
| EM | 000345483.003 | 7/2005 |
| EM | 000386388.0001 | 11/2005 |
| EM | 000386388.0002 | 11/2005 |
| EM | 000386388.0020 | 11/2005 |
| EM | 000386388.0028 | 11/2005 |
| EM | 000386388.0030 | 11/2005 |
| EM | 000386388.0031 | 11/2005 |
| EM | 000386388.0034 | 11/2005 |
| EM | 000500418.001 | 5/2006 |
| EM | 000540869.0021 | 7/2006 |
| EM | 000540869.0024 | 7/2006 |
| EM | 000603808.002 | 11/2006 |
| EM | 000623202.0002 | 12/2006 |
| EM | 000623202.0004 | 12/2006 |
| EM | 000623202.0009 | 12/2006 |
| EM | 000623202.0010 | 12/2006 |
| EM | 000623202.0011 | 12/2006 |
| EM | 000623202.0012 | 12/2006 |
| EM | 000623202.0013 | 12/2006 |
| EM | 000614706.001 | 1/2007 |
| EM | 000654272.0003 | 4/2007 |
| EM | 000654272.0004 | 4/2007 |
| EM | 000654272.0005 | 4/2007 |
| EM | 000688007.0002 | 4/2007 |
| EM | 000688007.0003 | 4/2007 |
| EM | 000871017.0001 | 2/2008 |
| EM | 000871017.0007 | 2/2008 |
| EM | 000871017.0008 | 2/2008 |
| EM | 000871017.0009 | 2/2008 |
| EM | 000871017.0010 | 2/2008 |
| EM | 000871017.0014 | 2/2008 |
| EM | 000871017.0015 | 2/2008 |
| EM | 000871017.0016 | 2/2008 |
| EM | 000871017.0024 | 2/2008 |
| EM | 000871017.0025 | 2/2008 |
| EM | 000871017.0026 | 2/2008 |
| EM | 000871017.0027 | 2/2008 |
| EM | 000871017.0028 | 2/2008 |
| EM | 000871017.0029 | 2/2008 |
| EM | 000871017.0030 | 2/2008 |
| EM | 000871017.0031 | 2/2008 |
| EM | 000871017.0032 | 2/2008 |
| EM | 000871017.0033 | 2/2008 |
| EM | 000871017.0037 | 2/2008 |
| EM | 000871017.0038 | 2/2008 |
| EM | 000871017.0039 | 2/2008 |
| EM | 000871017.0040 | 2/2008 |
| EM | 000871017.0043 | 2/2008 |
| EM | 000871017.0044 | 2/2008 |
| EM | 000871017.0054 | 2/2008 |
| EM | 000871017.0055 | 2/2008 |
| EM | 000871017.0056 | 2/2008 |
| EM | 000871017.0057 | 2/2008 |
| EM | 000871017.0058 | 2/2008 |
| EM | 000871017.0059 | 2/2008 |
| EM | 000871017.0060 | 2/2008 |
| EM | 000871017.0061 | 2/2008 |
| EP | 0024365 A2 | 3/1981 |
| EP | 0024365 B1 | 3/1981 |
| EP | 549494 | 6/1993 |
| EP | 1064920 A1 | 1/2001 |
| EP | 997135 B1 | 9/2001 |
| EP | 1238603 A3 | 9/2003 |
| EP | 1452164 B1 | 12/2007 |
| EP | 2084387 A1 | 8/2009 |
| EP | 2091612 A1 | 8/2009 |
| EP | 2117497 A2 | 11/2009 |
| FR | 2079785 | 10/1971 |
| FR | 000975286.0001 | 12/1997 |
| FR | 2898469 A1 | 9/2007 |
| FR | 2919477 A1 | 2/2009 |
| GB | 2124081 A | 9/1985 |
| GB | 2293545 A | 4/1996 |
| JP | 03173811 | 7/1991 |
| JP | 11-504324 A | 4/1999 |
| JP | 3173811 A | 7/2001 |
| JP | 2002-154932 A | 5/2002 |
| JP | 2003-183131 A | 7/2003 |
| JP | 2004-155768 A | 6/2004 |
| JP | 2004188189 A | 7/2004 |
| JP | 2004238363 A | 8/2004 |
| JP | 2004339212 A | 12/2004 |
| JP | 3619981 B2 | 2/2005 |
| JP | 3794320 B2 | 7/2006 |
| JP | 2006174936 A | 7/2006 |
| JP | 2006282585 | 10/2006 |
| JP | 0D1207926 | 5/2007 |
| JP | 2009114099 A | 5/2009 |
| JP | 2009137841 A | 6/2009 |
| JP | 2009-227592 A | 10/2009 |
| JP | 4813034 B2 | 11/2011 |
| KR | 300402225.0000 | 12/2005 |
| KR | 300405136.0000 | 2/2006 |
| KR | 300424071.0001 | 2/2006 |
| KR | 300465977.0000 | 10/2007 |
| KR | 300488446.0000 | 4/2008 |
| KR | 300507379.0000 | 9/2008 |
| WO | WO-000011033.0003 | 7/1988 |
| WO | WO-000014434.0010 | 10/1989 |
| WO | WO-000014434.0011 | 10/1989 |
| WO | WO-000014434.0025 | 10/1989 |
| WO | 1996/20698 | 7/1996 |
| WO | WO-000042185.0001 | 2/1998 |
| WO | WO-000042185.0002 | 2/1998 |
| WO | WO-000042185.0003 | 2/1998 |
| WO | WO-000042185.0004 | 2/1998 |
| WO | 2000/47177 | 8/2000 |
| WO | WO-000054973.0006 | 3/2001 |
| WO | 2001/45652 | 6/2001 |
| WO | 2004073662 A1 | 9/2004 |
| WO | WO2006058795 A1 | 6/2006 |
| WO | 2006/078541 | 7/2006 |
| WO | 2006/137383 A1 | 12/2006 |
| WO | WO2007/040517 * 4/2007 | ............ A61Q 1/10 |
| WO | WO2007015166 A2 | 4/2007 |
| WO | WO2007031872 A2 | 9/2007 |
| WO | WO2008074844 A1 | 6/2008 |
| WO | 2008089926 A | 7/2008 |
| WO | WO2008074850 A2 | 10/2008 |
| WO | WO2008074870 A2 | 10/2008 |
| WO | WO-2009/086338 A1 | 7/2009 |
| WO | WO-2011/056562 A2 | 5/2011 |
| WO | WO-2011/114099 A1 | 9/2011 |
| WO | WO-2012/011043 A1 | 1/2012 |
| WO | WO-2012/058095 A1 | 5/2012 |
| WO | WO-2013/163502 A1 | 10/2013 |
| WO | WO 2017/044548 A1 | 3/2017 |

(56) References Cited

FOREIGN PATENT DOCUMENTS

OTHER PUBLICATIONS

U.S. Appl. No. 13/046,014, filed Mar. 11, 2011, Gwen Sheila Trinidad Aceirto, et al.
PCT International Search Report and Written Opinion for PCT/US2013/038339 dated Sep. 12, 2013.
R. Pigeon and P. Allard, Chimie Macromo-culaire Applique, 40141 (1974), pp. 139-158 (No. 600).
PCT International Search Report and Written Opinion for PCT/US2012/038231 dated Aug. 21, 2012.
Avon, Avon Colour, In a Blink Eye Shadow and Liner, date published Mar. 2007; www.gnpd.com, 2 pages.
Avon, Avon, Blueberry Cool/Black Lush Lips and Long Lashes, date published Mar. 2006; www.gnpd.com, 2 pages.
Avon, Avon, Dual Ended Eye-Liner, date published Oct. 2007; www.gnpd.com, 2 pages.
Avon, Avon, Shimmer Shadow and Liner, date published Jun. 2007; www.gnpd.com, 2 pages.
Avon, MistakeProof Mascara, date published Oct. 2008; www.gnpd.com , 4pages.
Bare Escentuals, bareMinerals Tutorials, Lesson 1: Get Cheeky, date published Feb. 2008; www.gnpd.com, 1 page.
Bare Escentuals, bareMinerals, Get Started: Eyes, Cheeks, Lips Set, date published Mar. 2008; www.gnpd.com, 1 page.
Bobbi Brown Copper Diamond, Everything/Lash Glamour Mascara Duo, date published Nov. 2008; www.gnpd.com, 3 pages.
Bobbi Brown, Bobbi Brown Christmas 2008, Night Sky Long-Wear Eye Palette, date published Dec. 2008; www.gnpd.com, 3 pages.
Bobbi Brown, Honey Glaze Long-Wear Eye Palette, date published Apr. 2009; www.gnpd.com, 3 pages.
Bobbi Brown, Lip and Eye Basics Palette, date published Sep. 2006; www.gnpd.com, 2 pages.
Bobbi Brown, Shimmering Nudes Collection, Shimmering Nudes Palette, date published Oct. 2008; www.gnpd.com, 3 pages.
Caboodles Color Tips, Mascara Extension, date published Dec. 2005; www.gnpd.com, 2 pages.
Cosmetobelleza Natural IM , Double Effect Mascara, date published: Jul. 2009; www.gnpd.com, 2 pages.
Creative Brands, Australis, Eyeshadow, date published Aug. 2007; www.gnpd.com, 2 pages.
Del Laboratories, Sally Hansen Healing Beauty, Thicken-Up Plumper + Mascara, date published Oct. 2003; www.gnpd.com, 2 pages.
Gurwitch Products, Laura Mercier, Limited-Edition Eye Book, date published Dec. 2008; www.gnpd.com, 2 pages.
Gurwitch Products, Laura Mercier, Beauty Library Set, date published Dec. 2006; www.gnpd.com, 3 pages.
Helena Rubinstein, Surrealist Mascara & Liner, date published Nov. 2006; www.gnpd.com, 2 pages.
Invima, Isadora Wonder Full Mascara, date published Sep. 2006; www.gnpd.com, 2 pages.
Kao, Aube Couture, Designing Double Mascara, date published Dec. 2008; www.gnpd.com, 3 pages.
Isehan, Kiss Me Mascara Remover, date published Sep. 2008; wwww.gnpd.com, 2 pages.
Kose, Fasio Easy Mascara Remover, date published Jun. 2009; wwww.gnpd.com, 3 pages.
Kose, Fasio Mascara Easy Remover, date published Jan. 2009; wwww.gnpd.com, 2 pages.
Lorac Cosmestics, Lorac, Fairytale Life Makeup Collection, date published Dec. 2007; www.gnpd.com; 4 pages.
L'Oréal Double Mascara, Date published May 2006; www.gnpd.com, 2 pages.
MAQuillAGE Shiseido, Mascara Remover, date published Jun. 2008; wwww.gnpd.com, 2 pages.
Napoleon Perdis Cosmetics, NP Set Eyeliner, date published Mar. 2009; www.gnpd.com, 4 pages.
Napoleon Perdis Cosmetics, NP Set, Eye Palette, date published Feb. 2009 www.gnpd.com, 3 pages.
Prestige Cosmetics, Glitter Lash Mascara, date published Dec. 2008, www.gnpd.com, 2 pages.
Revlon, Limited Edition Dual Lash Mystique Mascara, date published Jun. 2003; www.gnpd.com, 1 page.
Rimmel , Coty, Volume Extend Waterproof Mascara, date published Sep. 2006; www.gnpd.com, 2 pages.
Rimmel, Double Play Multi Look Mascara, date published Apr. 2007; Mar. 2007; www.gnpd.com, 2 pages.
Rossman, Rival de Loop Young, Double Brush Mascara, date published: Oct. 2009; www.gnpd.com, 2 pages.
Shiseido, The Makeup Eraser Pencil, date published Jun. 2001; wwww.gnpd.com, 2 pages.
Sleek Makeup, Duo Dip It Mascara + Eyeliner, date published Mar. 27, 2009; www.gnpd.com, 3 pages.
SmashBox Limitless Lash Mascara, date published May 2003 wwww.gnpd.com, 2 pages.
Swab Plus Eye Makeup Remover Swabs , date published Nov. 2007; wwww.gnpd.com, 2 pages.
SwabPlus Waterproof Mascara Remover Swabs, date published Dec. 2002; www.gnpd.com, 2 pages.
Tarte Cosmetics, Tarte Fall 2008, Eye Couture Day-to-Night Eye Palette, date published Aug. 2008; www.gnpd.com, 2 pages.
The Art of Makeup, VIP Complete Cosmetic Kit, date published Feb. 2008; www.gnpd.com 4 pages.
Narus Cosmetics, Wink Up Mascara Remover, date published Mar. 1999; wwww.gnpd.com, 1 page.
Xtreme Color, Mary-Kate and Ashley, Eye Drama Creme Eye Color Plus Rich Mascara, date published Jul. 2004; wwww.gnpd.com, 2 pages.
Yves Saint Laurent; Yves Saint Laurent Parfums; Duo Expert Sourcils, date published Nov. 2004; www.gnpd.com, 1 page.
PCT International Search Report and Written Opinion for PCT/US2013/041135 date Nov. 8, 2013.
PCT International Search Report and Written Opinion for PCT/US2010/054090 date Feb. 16, 2012.
PCT International Search Report and Written Opinion for PCT/US2010/054089 date Feb. 16, 2012.
PCT International Search Report and Written Opinion for PCT/US2010/054085 dates Feb. 23, 2012.
PCT International Search Report and Written Opinion for PCT/IB2008/050102 dated Jun. 9, 2008.
PCT International Search Report and Written Opinion for PCT/US2010/054079 date Feb. 23, 2012.
PCT International Search Report and Written Opinion for PCT/US2011/033429 date Jun. 1, 2011.
PCT International Search Report and Written Opinion for PCT/US2011/057104 dated Feb. 21, 2012.
R.E. Lobnig et al., "Development of a new experimental method to determine critical pigment-volume-concentrations using impedance spectroscopy", Progress in Organic Coatings 55 (2006) 363-374.
J. Jachowicz et al., "The effect of the amphiprotic nature of human hair keratin on the adsorption of high charge density cationic polyelectrolytes", Colloid and Polymer Science 263: 847-858 (1985).
S.H.M. Gibson et al., "Determination of the critical pigment volume contrations of pigmented film coating formulations using gloss measurement", International Journal of Pharmaceutics 45, (1988) 245-248.
F. Zulli et al., "Preparation and properties of small nano particles for skin and hair care", SOFW Journal 123, Jahrgang 13/97 p. 880-885.
Masaki Okazaki et al., "Introduction of cationic groups onto carbon black surface and their dispersibility in water", J. Dispersion Science and Technology 21(5), 511-524 (2000).
U.S. Appl. No. 13/894,665, filed May 15, 2013, Hodgetts et al.
"U.S. Appl. No. 15/259,089, Non Final Office Action dated Nov. 1, 2017", 13 pgs.
"Japanese Application Serial No. 2016-155058, filed Sep. 21, 2017 to Office Action dated Jun. 8, 2017", (w/ English Translation of Claims), 9 pgs.
"U.S. Appl. No. 13/457,173, Final Office Action dated Jan. 13, 2015", 11 pgs.
"U.S. Appl. No. 13/457,173, Final Office Action dated Jun. 20, 2014", 13 pgs.

(56) References Cited

OTHER PUBLICATIONS

"U.S. Appl. No. 13/457,173, Non Final Office Action dated Jul. 9, 2015", 14 pgs.
"U.S. Appl. No. 13/457,173, Non Final Office Action dated Sep. 26, 2014", 11 pgs.
"U.S. Appl. No. 13/457,173, Non Final Office Action dated Dec. 5, 2013", 11 pgs.
"U.S. Appl. No. 13/457,1 d3, Notice of Allowance dated Sep. 30, 2015", 7 pgs.
"U.S. Appl. No. 13/457,173, filed May 5, 2014 to Non Final Office Action dated Dec. 5, 2013", 8 pgs.
"U.S. Appl. No. 13/457,173, filed Jun. 2, 2015 to Final Office Action dated Jan. 13, 2015", 8 pgs.
"U.S. Appl. No. 13/457,173, filed Sep. 18, 2014 to Final Office Action dated Jun. 20, 2014", 10 pgs.
"U.S. Appl. No. 13/457,173, filed Sep. 21, 2015 to Non Final Office Action dated Jul. 9, 2015", 6 pgs.
"U.S. Appl. No. 13/457,173, filed Dec. 26, 2014 to Non Final Office Action dated Sep. 26, 2014", 7 pgs.
"U.S. Appl. No. 13/457,252, 312 Amendment dated Dec. 1, 2015", 3 pgs.
"U.S. Appl. No. 13/457,252, Final Office Action dated Jan. 13, 2015", 14 pgs.
"U.S. Appl. No. 13/457,252, Final Office Action dated Feb. 20, 2014", 16 pgs.
"U.S. Appl. No. 13/457,252, Final Office Action dated Apr. 19, 2013", 15 pgs.
"U.S. Appl. No. 13/457,252, Non Final Office Action dated Jul. 7, 2015", 14 pgs.
"U.S. Appl. No. 13/457,252, Non Final Office Action dated Sep. 29, 2014", 14 pgs.
"U.S. Appl. No. 13/457,252, Non Final Office Action dated Oct. 15, 2012", 15 pgs.
"U.S. Appl. No. 13/457,252, Non Final Office Action dated Nov. 1, 2013", 14 pgs.
"U.S. Appl. No. 13/457,252, Notice of Allowance dated Sep. 24, 2015", 7 pgs.
"U.S. Appl. No. 13/457,252, filed Jan. 30, 2014 to Non Final Office Action dated Nov. 1, 2013", 9 pgs.
"U.S. Appl. No. 13/457,252, filed Apr. 15, 2013 to Non Final Office Action dated Oct. 15, 2012", 8 pgs.
"U.S. Appl. No. 13/457,252, filed Jun. 2, 2015 to Final Office Action dated Jan. 13, 2015", 9 pgs.
"U.S. Appl. No. 13/457,252, filed Sep. 14, 2015 to Non Final Office Action dated Jul. 7, 2015", 7 pgs.
"U.S. Appl. No. 13/457,252, filed Sep. 18, 2014 to Final Office Action dated Feb. 20, 2014", 11 pgs.
"U.S. Appl. No. 13/457,252, filed Oct. 21, 2013 to Final Office Action dated Apr. 19, 2013", 9 pgs.
"U.S. Appl. No. 13/457,252, filed Dec. 26, 2014 to Non Final Office Action dated Sep. 29, 2014", 7 pgs.
"Canadian Application Serial No. 2,815,996, Notice of Allowance dated Sep. 17, 2015", 1 pg.
"Canadian Application Serial No. 2,815,996, Office Action dated Sep. 23, 2014", 3 pgs.
"Canadian Application Serial No. 2,815,996, Response filed Mar. 17, 2015 to Office Action dated Sep. 23, 2014", 12 pgs.
"Canadian Application Serial No. 2,815,996, Voluntary Amendment dated Apr. 25, 2013", 3 pgs.
"Canadian Application Serial No. 2,869,926, Notice of Allowance dated Jun. 22, 2016", 1 pg.
"Canadian Application Serial No. 2,869,926, Office Action dated Oct. 13, 2015", 6 pgs.
"Canadian Application Serial No. 2,869,926, Response filed Mar. 29, 2016 to Office Action dated Oct. 13, 2015", 15 pgs.
"Canadian Application Serial No. 2,869,926, Voluntary Amendment dated Oct. 7, 2014", 4 pgs.
"Chinese Application No. 201180051606.2, Argument and Amendment filed Dec. 24, 2014 in response to Office Action dated Jun. 18, 2014", (w. English Translation of Argument), 7 pgs.
"Chinese Application No. 201180051606.2, Office Action dated Apr. 28, 2015", (w/ English Translation), 7 pgs.
"Chinese Application No. 201180051606.2, Office Action dated Jun. 18, 2014", (w/ English Translation), 13 pgs.
"Chinese Application Serial No. 201380021259.8, Office Action dated Jan. 18, 2016", (w/ English Translation), 17 pgs.
"Chinese Application Serial No. 201380021259.8, Office Action dated Sep. 13, 2016", (w/ English Translation), 7 pgs.
"Chinese Application Serial No. 201380021259.8, Response filed Jan. 22, 2017 to Office Action dated Sep. 13, 2016", (w/ English Translation of Amended Claims), 12 pgs.
"Chinese Application Serial No. 201380021259.8, Response filed Aug. 2, 2016 to Office Action dated Jan. 18, 2016", (w/ English Translation of Amended Claims), 37 pgs.
"European Application Serial No. 11778749.9, Communication Pursuant to Article 94(3) EPC dated Mar. 23, 2016", 3 pgs.
"European Application Serial No. 11778749.9, Communication Pursuant to Article 94(3) EPC dated Aug. 16, 2016", 4 pgs.
"European Application Serial No. 11778749.9, Communication Pursuant to Article 94(3) EPC dated Oct. 2, 2014", 3 pgs.
"European Application Serial No. 11778749.9, Communication Pursuant to Article 94(3) EPC dated Oct. 22, 2015", 3 pgs.
"European Application Serial No. 11778749.9, Reply filed Feb. 21, 2017 to Communication Pursuant to Article 94(3) EPC dated Aug. 16, 16", 6 pgs.
"European Application Serial No. 11778749.9, Response filed Feb. 10, 2015 to Communication Pursuant to Article 94(3) EPC dated Oct. 2, 2014", 9 pgs.
"European Application Serial No. 11778749.9, Response filed Feb. 29, 2016 to Communication Pursuant to Article 94(3) EPC dated Oct. 2, 2014", 13 pgs.
"European Application Serial No. 11778749.9, Response filed May 26, 2016 to Communication Pursuant to Article 94(3) EPC dated Mar. 23, 2016", 6 pgs.
"European Application Serial No. 11778749.9, Response filed Dec. 9, 2013 to Communication pursuant to Rules 161(1) and 162 EPC dated Jun. 5, 2013", 8 pgs.
"European Application Serial No. 13720728.8, Response filed Jul. 29, 2015 to Communication pursuant to Rules 161(1) and 162 EPC dated Jan. 21, 2015", 14 pgs.
"International Application Serial No. PCT/US2011/057104, International Preliminary Report on Patentability dated May 10, 2013", 8 pgs.
"International Application Serial No. PCT/US2013/038339, International Preliminary Report on Patentability dated Nov. 6, 2014", 7 pgs.
"International Application Serial No. PCT/US2016/050651, International Search Report dated Nov. 18, 2016", 3 pgs.
"International Application Serial No. PCT/US2016/050651, Written Opinion dated Nov. 18, 2016", 7 pgs.
"Japanese Application Serial No. 2013-536678, Office Action dated Jun. 23, 2015", (w/ English Translation), 9 pgs.
"Japanese Application Serial No. 2013-536678, Office Action dated Jul. 1, 2014", (w/ English Translation), 24 pgs.
"Japanese Application Serial No. 2013-536678, Written Argument and Amendment filed Dec. 26, 2014 in response to Office Action dated Jul. 1, 2014", (w/ English Translation), 16 pgs.
"Japanese Application Serial No. 2016-155058, Office Action dated Jun. 8, 2017", (w/ English Translation), 8 pgs.
Todd, Charles, et al., "Volatile Silicone Fluids for Cosmetics", *Cosmetics and Toiletries*, 91, (1976), 29-32.
"U.S. Appl. No. 15/259,089, filed Jan. 26, 2018 to Non-Final Office Action dated Nov. 1, 2017", 13 pgs.
"U.S. Appl. No. 15/259,089, Final Office Action dated Mar. 22, 2018", 14 pgs.

\* cited by examiner

SEMI-PERMANENT MASCARA COMPOSITIONS

CROSS REFERENCE TO RELATED APPLICATION

This application claims the benefit of provisional application No. 61/455,843, filed Oct. 27, 2010.

FIELD OF THE INVENTION

Disclosed generally herein are semi-permanent cosmetic compositions and methods of removal. In particular, mascara that can last on the eyelashes, eyebrows, and/or eyelids in excess of 24 hours.

BACKGROUND OF THE INVENTION

Enhancing the beauty of one's eyes is of significant importance to consumers and has led to the development of very large product categories in both cosmetics and skin care. In particular, enhancing the visibility of eyelashes has become a multi billion dollar industry and continues to grow. Mascara is used to enhance the beauty of a person's eyes by coating the lashes to thicken, lengthen, and darken the eyelashes. As a result, consumers tend to be very passionate about their mascara, often stating that it is the one cosmetic product that provides the biggest impact on overall appearance. In fact, many women feel self-conscious being seen without their mascara. Many women would like their mascara beauty benefits to be available all day, every day.

There are generally two types of mascara, water resistant and waterproof. Water resistant mascara can be removed with warm water and soap, while waterproof mascara is typically removed with a make-up remover product. Both types are typically applied and removed during the same day. This leaves many time-points in a consumer's life when she is not able to enjoy the beauty benefits of mascara. Though many consumers wish they could have the lash beauty that mascara provides all the time, current technologies do not allow for this because they are not durable enough to withstand typical wear insults like rubbing, washing, sweating and sleeping. To date, products promising multi-day benefits have acted more as either lash stains or dyes, which provide a lash darkening benefit but fail to provide fullness and length, or water-proof type "long-wear" mascaras that do not maintain the initial beauty look over multiple days. But "long" is a relative term, and existing long-wear mascaras are designed to eliminate reapplication during the day, but also to be easily removable by the user using soap and water or a make-up remover product. Current technologies do not last through showering and sleeping and are therefore not suitable for truly semi-permanent wear. Conventional lash stain products provide color but not the thickening benefits that consumers want from mascara products. Furthermore, the beauty look of such lash stain products tends to degrade rapidly after the first day of wear.

A new category of cosmetic is desired. Semi-permanent make up is being increasingly sought out by consumers who want to look more beautiful at all times—whether working around the house, working out at the gym, or swimming in a pool. It provides added confidence in their appearance, giving them a sense that they are always ready for what life brings them. And a semi-permanent mascara technology that provides full mascara benefits of long, dark beautiful lashes for multiple days is seen as a time saver as it does not require daily application or the frequent touch-ups of conventional technologies.

Accordingly, it would be desirable to provide a semi-permanent mascara that can withstand the environmental insults typically faced by a mascara in use for more than twenty-four hours. It would also be desirable to provide a semi-permanent mascara that can withstand exposure to water and soap during showering and facial cleansing. It would further be desirable to provide a semi-permanent mascara that exhibits good abrasion resistance.

SUMMARY OF THE INVENTION

In order to provide a solution to the problems above, disclosed herein is a semi-permanent mascara composition. The semi-permanent mascara composition comprises from about 17% to about 30%, by weight, of a film former selected from the group consisting of tall oil glycerides, pentaerythrityl rosinate, glyceryl rosinate, and the hydrogenated versions and mixtures thereof. The permanent mascara composition also includes from about 0.1% to about 14%, by weight, of a colorant, and from about 10% to about 15%, by weight, of disteardimonium hectorite. However, the semi-permanent mascara composition is free of wax.

DETAILED DESCRIPTION OF THE INVENTION

All percentages are by weight of the personal-care composition, unless otherwise specified. All ratios are weight ratios, unless specifically stated otherwise. All numeric ranges are inclusive of narrower ranges; delineated upper and lower range limits are interchangeable to create further ranges not explicitly delineated. The number of significant digits conveys neither limitation on the indicated amounts nor on the accuracy of the measurements. All measurements are understood to be made at 25° C. and at ambient conditions, where "ambient conditions" means conditions under one atmosphere of pressure and at 50% relative humidity.

"Mascara," "mascara formula," and "mascara composition," as used herein, mean a compound that is applied to eyelashes, eyelids, and/or eyebrows. Mascara compositions of the present invention may be formulated for topical application on mammalian keratinous tissue for use in skin-care, cosmetic, and hair-care products; non-limiting uses of which include antiperspirants, deodorants, lotions (e.g. hand lotion and body lotion), skin-care products (e.g., face and neck lotions, serums, sprays), sunless tanners, cosmetics (e.g., foundation, mascara, concealer, blush, lipstick, lip gloss, eyeliner, eye shadow, eyebrow pencil), hair dyes, after-shaves, razor moisturizing/lubricating strips, razor shave-gel bars, feminine-care products, oral-care products, and baby-care products. The methods of using any of the aforementioned compositions are also included within the meaning of mascara composition. "Keratinous tissue," as used herein, refers to keratin-containing layers disposed as the outermost protective covering of mammals which includes, but is not limited to, skin, hair, and nails.

Figure 3:
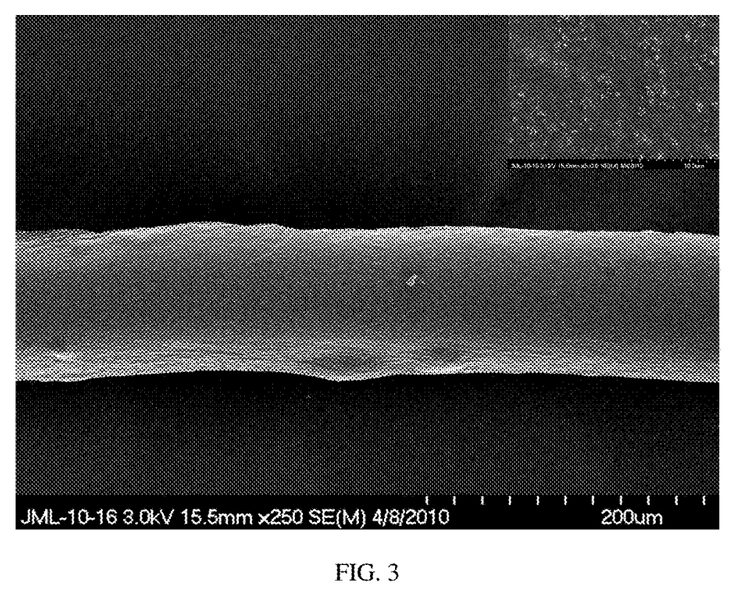
FIG. 3 is a 200×SEM image of the semi-permanent mascara film on a false eyelash showing continuous film with smooth surface; inset is at 5000×SEM.
Figure 4:
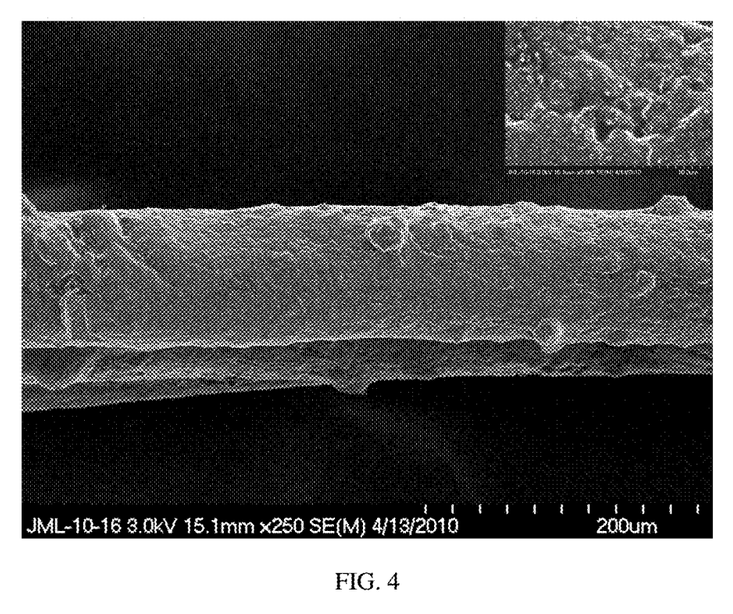
FIG. 4 is a 200×SEM image of Tarte 4 day Stay Lash Stain® film on a false eyelash showing discontinuous film with rough surface; inset 5000×SEM.
Figure 5:
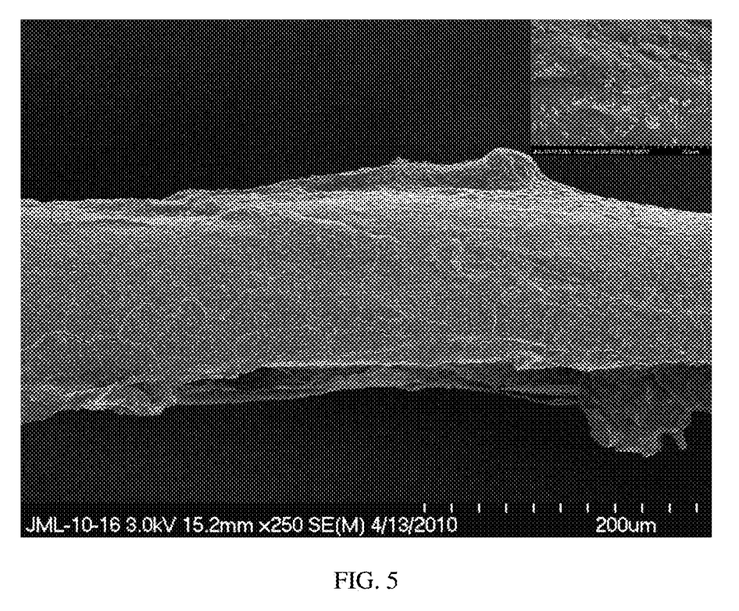
FIG. 5 is a 200×SEM image of Maybelline XXL Pro 24 HR Bold® film on a false eyelash showing discontinuous film with rough surface; inset 5000×SEM.
Figure 6:
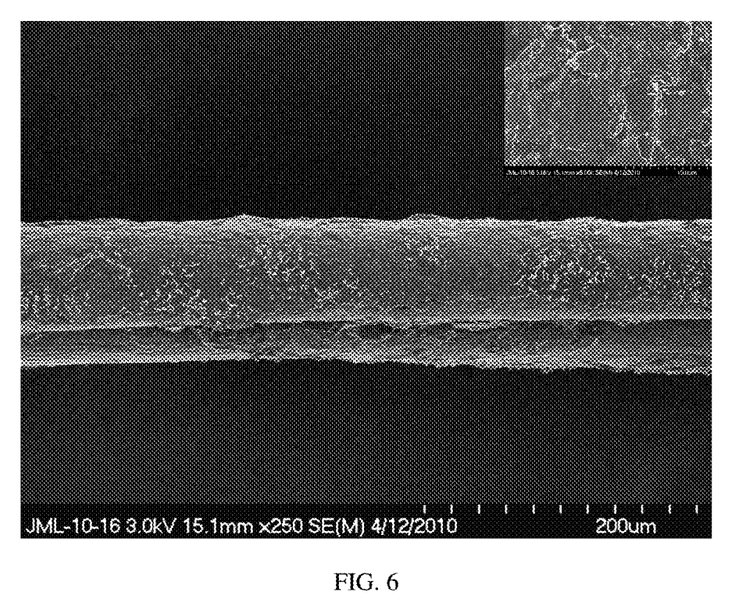
FIG. 6 is a 200×SEM image of CoverGirl® Lash Exact® film on a false eyelash showing discontinuous film with rough surface; inset 5000×SEM.

"Smooth" when used in reference to a film means the surface of the film is substantially free of crack-like discontinuities caused by particulates protruding out of the surface of the film surface when the film is viewed at 200× magnification. Examples of smooth films are discussed in more detail below and in particular with regard to FIG. 3. Examples of films that are not smooth are also discussed in more detail below and in particular with regard to FIGS. 4-6.

Semi-Permanent Mascara Formula

The present invention relates to a semi-permanent mascara formula that remains intact on the eyelashes and/or eyelids of the wearer for greater than 24 hours, preferably greater than 36 hours, and even more preferably greater than 48 hours. The new semi-permanent mascara formula achieves a multiple day wear benefit through two formula design elements. The first element is the choice of film-forming polymers. A broad range of polymers were screened for film flexibility, abrasion resistance, and water and surfactant resistance. The rosinate polymers used in the formula were found to have the best combination of these properties.

The second element is balancing the ratio of film-forming polymer to other non-volatiles in the formula such that there is sufficient polymer to form a continuous phase. The paint industry has recognized that the properties of a film are directly related to the volume concentration of solids it contains since the introduction of the concept of critical pigment volume concentration (CPVC) in 1949 by Asbeck and Van Loo. The CPCV is the point at which there is just sufficient polymer matrix to wet and fill the voids between individual particles. At volume concentrations above the CPVC, the polymer matrix is no longer a continuous phase. Decreasing the particle size of the solids increases the CPVC for a given system. Studies have shown that the pigment volume concentration impacts many film properties, including gloss, film flexibility and abrasion resistance. As the pigment volume concentration increases, film flexibility decreases and abrasion resistance remains the same or improves. When the CPVC is exceeded, the film will become brittle and abrasion resistance will decrease rapidly. Gloss also decreases as the pigment volume concentration increases and remains low when the CPVC is exceeded.

Current mascara formulations use large amounts of waxes (5-15%) and iron oxides (6-12%) while using relatively small amounts of film forming polymers (4-8%). The films that they form are dominated by the waxes which can have crystal sizes in excess of 20 microns and are jagged and rough in appearance. The pigments used are also relatively large and have a wide distribution of particle sizes, usually in the 2-5 micron range. Because they use large particulates and a relatively low amount of polymer, current mascaras have a solids volume concentration in excess of the CPVC. As a result, current mascara films exhibit poor abrasion resistance and often are very brittle films which flake very easily.

Figure 1:
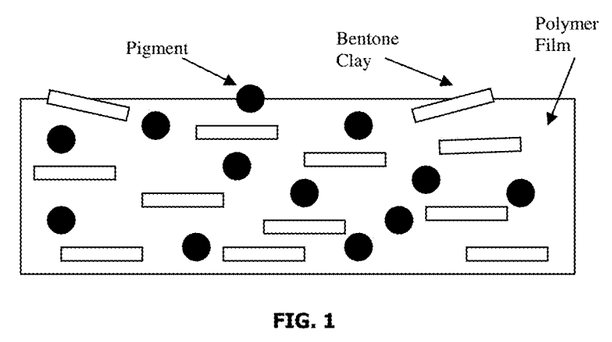
FIG. 1 is a schematic of a hypothesized film structure of the present semi-permanent composition.
Figure 2:
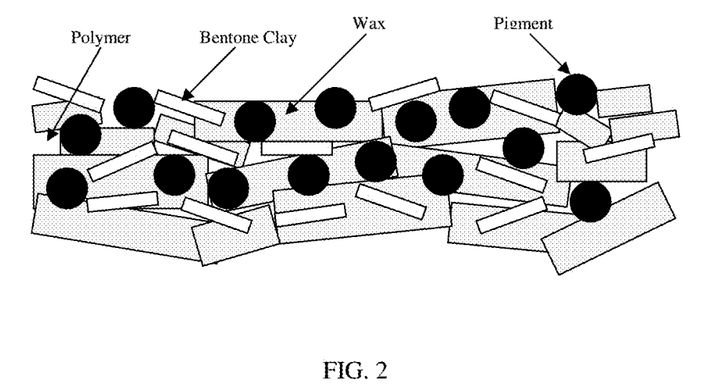
FIG. 2 is a schematic of a hypothesized film structure of a conventional mascara.

The new semi-permanent formula technology was designed so that the volume concentration of solids is below the CPVC. This was achieved in two ways. First, only small particle size solids were used for both the pigments and thickeners. In a preferred embodiment, the new formula technology is thickened using only disteardimonium hectorite clay particles (D90<10 microns) from 10% to 15% by weight of the composition, and colored with jet milled iron oxides (D90<1 micron) from 7% to 10% by weight of the composition. Minimizing the size of all particulates in the system increased the CPVC for the new mascara technology well above that of conventional mascaras. Second, in a preferred embodiment, a much greater level of film-forming polymers was used (17-30%) which ensured that the new mascara is well below the CPVC. The new semi-permanent formula technology forms a continuous polymer film with a smooth surface. Because its solids volume concentration is below the CPVC, it has much greater resistance to flaking and transfer caused by stretching and abrading than any current mascara technology. An additional benefit of the continuous film structure of the new mascara formula technology is that the film surface is smooth, resulting in a very glossy, very dark film appearance. The hypothesized film structure of the new semi-permanent formula technology is shown in FIG. 1. The hypothesized film structure of the current mascara formula technology is shown in FIG. 2.

Similar to many "waterproof" mascara formulas, the inventive semi-permanent mascara is an anhydrous dispersion (not emulsion) comprised of colorant particles dispersed in a matrix of film former(s) and volatile solvent(s). In one embodiment, the new semi-permanent formula technology is an anhydrous dispersion comprising isododecane as a volatile carrier, a combination of rosinate polymers as film formers, and iron oxides as colorants. Preferably, the matrix is stabilized using a clay network. Key compositional elements and features are outlined below.

Film-Forming Polymer

An essential component of the invention is a film-forming polymer from a class of rosinates or rosin esters. In a preferred embodiment, the semi-permanent mascara composition comprises film formers chosen from the group consisting of tall oil glycerides, pentaerythrityl rosinate, glyceryl rosinate, and mixtures thereof. These materials are derived from rosin. Rosin is a solid form of resin obtained from conifers, produced by heating liquid resin to vaporize the volatile liquid terpene components. It primarily consists of different resin acids, especially abietic acid. Rosin is typically obtained commercially either by distillation of volatile turpentine from oleoresin exuded from the wound of living pine trees to obtain gum rosin or the separation of tall oil, a byproduct of the wood pulp industry, to obtain tall oil rosin.

The carboxylic acid group of a rosin acid can be converted to an ester through a reaction with various alcohols. Esterification of rosin modifies the softening point, adhesiveness, cohesiveness, and melted viscosity of the material. The alcohols typically used to make rosin esters are methanol, tri-ethylene-glycol, glycerol, and pentaerythritol. Tall oil rosin is esterified with glycerol to form tall oil glycerides, a mixture of resin acids, rosin acids, and esters of glycerol. Tall oil glycerides are available from, for example, Arizona Chemical Co. Glyceryl Rosinate, is the ester of rosin acids with glycerol. Pentaerythrityl rosinate, sometimes referred to as pentaerythritol rosinate, is the ester of rosin acids with pentaerythritol. It is used as a skin conditioning agent-emollient and viscosity increasing agent-nonaqueous in a few cosmetic formulations. Pentaterythrityl Rosinate is commercially available, for example, from Eastman.

Rosin's conjugated double bond makes it susceptible to oxidation, isomerization and other reactions. A common method to improve stability is to hydrogenate the rosin molecules. This is done by the addition of hydrogen to double bonds in the resin acid, typically catalyzed by nickel compounds or noble metals to form saturated ring structures. Hydrogenation greatly increases the molecule's resistance to oxidation and improves its color. The hydrogenation process can be controlled so that the rosin is either partially or fully hydrogenated. Hydrogenated rosins have specific advantages over non-hydrogenated rosin resins including lighter color, improved stability, and reduced skin sensitization. The hydrogenated versions of pentaerythrityl rosinate and glyceryl rosinate, pentaerythrityl hydrogenated rosinate (PHR) and glyceryl hydrogenated rosinate (GHR) may be used in the invention.

Film formers such as tall oil glycerides, pentaerythrityl rosinate, pentaerythrityl hydrogenated rosinate, glyceryl rosinate, and glyceryl hydrogenated rosinate are used in the present invention in higher concentration than previously used in mascara. The semi-permanent mascara formula comprises at least 15%, preferably at least 17%, and even more preferably at least 20% up to between 30% and 35%, by weight, of a film former selected from the group consisting of tall oil glyceride, pentaerythrityl rosinate, glyceryl rosinate, and the hydrogenated versions and mixtures thereof. The ratio of film former to volatile carrier is controlled such that the dried film consists of from 30% to 70% film former by weight, preferably from 40% to 60%, and most preferably 50%.

Carrier Solvents

The semi-permanent mascara composition comprises a carrier solvent to achieve delivery of the film formers to the eyelash or eyelid. In a preferred embodiment, the semi-permanent mascara composition comprises a volatile carrier which quickly volatilizes from the surface of the eyelashes or eyelid, leaving the desired components behind. The volatile carrier comprises from 10% to 85%, preferably from 15% to 80%, and most preferably from 20% to 70% of the composition. The volatile carrier of the present invention is selected from the group consisting of volatile hydrocarbons, volatile silicones and mixtures thereof.

Hydrocarbon oils useful in the present invention include those having boiling points in the range of 60-260° C., more preferably hydrocarbon oils having from C8 to C20 chain lengths, most preferably C8 to C20 isoparaffins. Of these isoparaffins most preferred are selected from the group consisting of isododecane, isohexadecane, isoeicosane, 2,2,4-trimethylpentane, 2,3-dimethylhexane and mixtures thereof. Most preferred is isododecane, available as for example Permethyl 99A from Presperse corresponding to the formula:

Preferred volatile silicone fluids include cyclomethicones having 3, 4 and 5 membered ring structures corresponding to the formula:

where X is from 3 to 6. Said volatile silicones include 244 Fluid, 344 Fluid and 245 Fluid, and 345 Fluid all from Dow Corning Corporation.

Colorants

Colorants suitable for use in the present invention include, but are not limited to, a dye, pigment, lake, and mixture thereof. Typical suitable colorants for eye-area cosmetics include any organic or inorganic pigment or colorant approved for use in eye-area cosmetics by CTFA and/or the FDA such as lakes, iron oxides, titanium dioxide, iron sulfides, ultramarines or other conventional pigments used in cosmetic formulations.

Examples of pigments include inorganic pigments such as chromium oxide greens, ultramarines, yellow iron oxide, brown iron oxide, red iron oxide, and titanium oxide; and organic pigments such as D&C Black No. 2, D&C Black No. 3, FD&C Red No. 40, D&C Green No. 5, FD&C Blue No. 1, and FD&C Yellow No. 5. Examples of lake dyes include various acid dyes which are laked with aluminum, calcium or barium.

The above pigments, dyes, and lakes are well known, commercially available materials, with their chemical structure being described, e.g., in 21 C. F. R. Part 74 (as revised Apr. 1, 1988) and in the CTFA Cosmetic Ingredient Handbook, (1988), published by the Cosmetics, Toiletry and Fragrances Association, Inc.

Encapsulated colorant microparticles having average diameters of 0.1 to 10 microns are acceptable for use in the compositions of the present invention, for example 0.1 to 5 and especially 0.1 to 1 microns. The encapsulated colorant microparticles may comprise 1 to 60% by weight of at least one colorant, for example 5-40% and especially 7 to 25% by weight.

Additionally, the microencapsulated colorants may provide a more vibrant color to products used around the eye area, including eyelashes. The primary colors are understood to mean red, yellow and blue. An additional feature of microparticles is the elimination of milling or grinding often encountered with non-encapsulated colorants. Said colorants are preferably organic.

Colorants that are surface modified with a hydrophobic coating are acceptable for use in the compositions of the present invention, for example Triethoxycaprylsilane. Hydrophobically coating of colorants may increase their dispensability in the non-polar solvent and increase their resistance to being washed off during exposure to showering and facial cleansing.

The colorant for use herein is preferably selected from the following exemplary list of currently available colorants approved by the FDA for use around the eyes. Other colorants may also be used as they are developed and determined safe. Colorants for use in the present invention can be selected from the group consisting of annatto, caramel, carmine, β-carotene, bismuth oxychloride, iron oxides, ferric ammonium ferrocyanide, ferric ferrocyanide, chromium hydroxide green, chromium oxide greens, guanine, mica, titanium dioxide, aluminum powder, bronze powder, copper powder, ultramarines, manganese violet, zinc oxide, D&C Black No. 2, D&C Black No. 3, FD&C Blue No. 1, D&C Green No. 5, FD&C Red No. 40, and FD&C Yellow No. 5.

The semi-permanent mascara composition according to the invention comprises from 0.1 to 70% by weight, for example from 0.5 to 50% by weight, and especially from 0.5 to 35% by weight based on the total weight of the composition, of a colorant. Colorants having average diameters of 0.1 to 10 microns are acceptable for use in the compositions of the present invention, for example 0.1 to 5 and especially 0.1 to 1 microns. It is preferable that the diameter of the colorant is smaller than the thickness of the mascara composition dried-down film. The preferred diameter of the colorant is less than 1 micron. The small size of the colorants allows them to be fully encased in the dried film.

Thickeners

The semi-permanent mascara composition can be thickened or structured with colloidal particles such as disteardimonium hectorite, kaolin, silica, and magnesium carbonate; polymers; viscous hydrocarbons; and combinations thereof. Disteardimonium hectorite is the preferred thickener to build structure/viscosity. This enables proper spreading/deposition across lashes, and ensures adequate stability/suspension of colorant particles in dispersion over time. It is preferable that the diameter of the disteardimonium hectorite is smaller than the thickness of the mascara composition dried-down film. The preferred diameter of the disteardimonium hectorite is less than 10 microns. The semi-permanent mascara composition according to the present invention comprises from 1% to 25% disteardimonium hectorite, preferably from 2% to 20% disteardimonium hectorite, most preferably from 3% to 15% disteardimonium hectorite.

In less preferred embodiments, the semi-permanent mascara composition may include wax(es) such as, for example, waxes selected from the group consisting of carnauba wax, candellila wax, beeswax, and polyethylene wax. However, the presence of too much wax in the semi-permanent mascara composition may undesirably affect the semi-permanent characteristics of the wax by decreasing the abrasion resistance of the mascara. In certain embodiments the semi-permanent mascara composition includes less than 3.0%, less than 1.0%, or even less than 0.1%, by weight, of wax and/or wax like components. In certain embodiments, the semi-permanent mascara composition is free of wax.

Semi-Permanent Mascara Top Coat

A second composition may be placed over the semi-permanent mascara compositions of the present invention or over any commercially available mascara. These second, overlying compositions are referred to herein as a top coat. The preferred topcoat composition is anhydrous and designed to mitigate the tackiness of the base layer or basecoat as well as extend the wear of the product. A combination of semi-permanent mascara basecoat plus a semi-permanent topcoat may extend the longevity of the composition even longer than 24, 36, or 48 hours; the combination may enable the mascara to wear for three to five days.

An essential component of the top coat is a film forming polymer. One example of a film forming polymer suitable for use in the present invention is an organosiloxane resin. The film forming polymers can also be incorporated into the mascara composition described above. The resin may comprise combinations of R3SiO1/2 "M" units, R2SiO "D" units, RSiO3/2 "T" units, SiO2 "Q" units in ratios to each other that satisfy the relationship RnSiO(4−n)/2 where n is a value between 1.0 and 1.50 and R is a methyl group. Up to 5% of silanol or alkoxy functionality may also be present in the resin structure as a result of processing. The organosiloxane resins have a number molecular weight average range of from 1,000 g/mole to 10,000 g/mole. The resin is soluble in organic solvents such as toluene, xylene, isoparaffins, and cyclosiloxanes or the volatile carrier, indicating that the resin is not sufficiently crosslinked such that the resin is insoluble in the volatile carrier. Particularly preferred are resins comprising repeating monofunctional or R3SiO1/2 "M" units and the quadrafunctional or SiO2 "Q" units, otherwise known as "MQ" resins as disclosed in U.S. Pat. No. 5,330,747, Krzysik, issued Jul. 19, 1994, incorporated herein by reference. In the present invention the ratio of the "M" to "Q" functional units is 0.6 to 2.0, more preferably 0.6 to 0.9, most preferably 0.7. Examples of organosiloxane resins commercially available are Wacker 803 and 804 available from Wacker Silicones Corporation of Adrian, Mich., and G.E. SR1000 from the General Electric Company.

Organosiloxane resins are used in the present invention at levels from 10% to 95%, preferably from 55% to 80%, and most preferably 60% to 70% of the total amount of top coat composition. In one embodiment of this invention the top coat comprises less than 3.0%, preferably less than 1.0%, even more preferably less than 0.1%, by weight, of colorants.

In a preferred embodiment, isododecane is used as a volatile solvent. In a preferred embodiment, trimethylsiloxysilicate (MQ Resin) and dimethicone are used as film-forming agents. These ingredients were selected because in combination they form flexible and non-tacky films.

Mascara Remover

As discussed above, high concentrations of PHR and tall oils substantially reduce the solubility of the semi-permanent mascara in soap and water. Prior mascara formulations kept the concentration of these two components low to insure the mascara could be washed off in soap and water. Accordingly, in one aspect of this invention a solvent-based mascara-remover composition is provided. The mascara remover comprises at least 40%, preferably at least 50%, and even more preferably at least 55% of a solvent selected from the group consisting of mineral oil, petroleum jelly, isododecane, silicones, other hydrocarbon solvents and mixtures thereof. The solvent can comprise up to 100% of the remover composition.

Optional Ingredients

The semi-permanent mascara, top coat, and mascara remover described above may contain other optional ingredients. Because there is some overlap between the mascara, top coat, and remover compositions described above and the optional ingredients which may be included in them, the optional ingredients are described together below.

Actives

The compositions of the present invention may comprise a safe and effective amount of a biological, chemical, nutraceutical, or pharmaceutical active, or a combination thereof. Biological actives may include prostaglandins, antimicrobials, antibacterials, biocides, preservatives, proteins, amino acids, peptides, hormones, growth factors, enzymes (e.g., glutathione sulphydryl oxidase, transglutaminase), therapeutics, oligonucleotides, genetic materials (e.g., DNA, RNA), and combinations thereof. Chemical actives may include dyes, surfactants, sensates, hair conditioners, hair dyes, hair growth agents, hair removers, hair growth inhibitors, hair styling gels, and combinations thereof. Nutraceutical actives may include proteins, preservatives, vitamins, food-additive materials, and combinations thereof. Pharmaceutical actives may include antibiotics, drugs, hair growth agents, hair removers, hair growth inhibitors, and combinations thereof.

Oil Soluble or Oil Dispersible Additives

The choice of oil-soluble or dispersible additive and the amount present according to the invention will depend on the intended use of the composition and the effectiveness of the compound. In semi-permanent mascara, top coat and remover compositions, the oil-soluble or dispersible additive chosen is acceptable for skin and eye contact, as is well known to the skilled formulator. Suitable oil-soluble or dispersible additives are incorporated at levels generally between 1 and 20% by weight based on the weight of the matrix bead (equivalent to 90 to 300% on weight of the colorant). Preferably 5 to 15% by weight of the oil-soluble or dispersible additive is employed.

The oil-soluble or dispersible additive may include fatty alcohols such as GUERBET alcohols based on fatty alcohols having from 6 to 30, preferably from 10 to 20 carbon atoms including lauryl alcohol, cetyl alcohol, stearyl alcohol, cetearyl alcohol, oleyl alcohol, benzoates of $C_{12}$-$C_{15}$ alcohols, acetylated lanolin alcohol, etc. Especially suitable is stearyl alcohol. The oil-soluble or dispersible additive may include fatty acids such as Linear fatty acids of $C_6$-$C_{24}$, branched $C_6$-$C_{13}$-carboxylic acids, hydroxycarboxylic acids, caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerization of unsaturated fatty acids). Further components that can be used are dicarboxylic acids of $C_2$-$C_{12}$, such as adipic acid, succinic acid, and maleic acid. Aromatic carboxylic acids, saturated and/or unsaturated, especially benzoic acid, can be used. Additional components that can be used as the oil soluble or dispersible additive include carboxylic acid salts; alkaline soaps of sodium, potassium and ammonium; metallic soaps of calcium or magnesium; organic basis soaps such as lauric, palmitic, stearic and oleic acid, etc., alkyl phosphates or phosphoric acid esters: acid phosphate, diethanolamine phosphate, potassium cetyl phosphate.

Other useful oil-soluble or dispersible additives comprise mild surfactants, super-fatting agents, consistency regulators, additional thickeners, polymers, stabilizers, biologically active ingredients, deodorizing active ingredients, anti-dandruff agents, film formers, swelling agents, UV light-protective factors, antioxidants, preservatives, insect repellents, solubilizers, colorants, bacteria-inhibiting agents, hair conditioning agents, vitamins, and the like.

Packaging

The semi-permanent mascara composition of the present invention may be packaged alone or in combination with a basecoat, topcoat, remover, eyeliner, eyebrow product, or combination thereof. In one embodiment, a mascara kit comprises a double-ended package, wherein the first end contains a semi-permanent mascara composition of the present invention and wherein the second end contains a mascara-remover composition of the present invention. In another embodiment, a mascara kit comprises a double-ended package, wherein the first end contains a semi-permanent mascara composition of the present invention and wherein the second end contains a topcoat composition.

A semi-permanent mascara, basecoat, topcoat, eyeliner, or eyebrow-product package (or complementary advertising) of the present invention may comprise indicia which suggests the long-wearing nature of the mascara composition. For instance, the indicia may comprise a certain number of hours the product may last, for example, 24 hours, 36 hours, or 48 hours. Or, the indicia may comprise a clock graphic. The indicia may be in a form selected from the group consisting of a label, a graphic, a three-dimensional shape, and combinations thereof. In one embodiment, the package comprises an hourglass indicia; the hourglass indicia may signal to the consumer that the product within is long-lasting. In a preferred embodiment, a mascara kit comprises a double-ended package, wherein the first end contains a semi-permanent mascara composition of the present invention and wherein the second end contains a mascara-remover composition of the present invention, and wherein the double-ended package comprises an indicia suggesting long-wear. Most preferably, the indicia comprises an hourglass.

Uses

In addition to the conventional mascara uses (e.g., coloring the lashes), the semi-permanent mascara composition or topcoat of the present invention may be used for additional functions. For example, the mascara described herein may be used as an eyeliner, an eyebrow pencil, an eyebrow styling gel, an eyebrow highlighter, a basecoat, a primer, an active-delivery system, etc. The semi-permanent mascara composition described may also be used to attach adornments to the face or specifically, around the eye area. For instance, the mascara composition of the present invention may be used to attach false lashes, glitter, rhinestones, feathers, jewelry, etc to the face or eye area. Furthermore, the mascara composition of the present invention may be modified to create semi-permanent face makeup, such as foundation, concealer, blush, lipstick, etc, or to create a body concealer (e.g., to cover tattoos, blemishes, veins, or bruises on various parts of the body, such as the legs and back). One of ordinary skill in the art will recognize that not all of these forms require the presence of a colorant, e.g., a composition to attach adornments or a brow styling gel may be clear.

Test Methods

In the Example section below, semi-permanent mascara compositions of the present invention are tested against current mascara compositions (products that are or were recently offered for sale to the public).

Rub Test Method

Equipment: 10"×5½" Leneta Form 2A Opacity Charts
    0.006" draw down bar
    Draw down board
    Kimberly-Clark "WypAll" L40 Paper towels
    2½" diameter 2 kg weight
    2½" diameter arch punch
    Scissors
    50° C. Oven
    Double sided tape
    Datacolor Microflash 200d Procedure:

1. Drawdown Preparation:
   a. Place a Leneta card on a drawdown board, Black/White side up. Label the top right of the card with sufficient sample & solvent identification. Take care to touch the card as little as possible since skin oils can affect the film thickness of product on the card.

b. Apply 1-2 ml of product in a line across the top of the card, and use a 0.006" drawdown bar to draw a film down the entire length of the card.
c. Repeat steps 1a & 1b for all products to be tested.
d. Once all draw downs have been completed, place them in a 50° C. oven for two hours.
Take care not to mar the film surfaces.
e. After an hour, remove the samples from the oven and allow them to equilibrate to ambient room temperature.
2. Sample Abrasion:
a. Use an arch punch to punch out 2½" diameter "abrasion substrate" disks from "WypAll" paper towels.
b. Completely and evenly, (do not overlap) apply strips of double sided tape to the bottom of a 2 kg weight. Cut away excess tape that extends beyond the perimeter of the weight bottom. Place and adhere a single WypAll disk (1 ply thickness) to the sticky bottom of the weight. This will be used to abrade the film and see how much of it is removed.
c. Place the disk/weight in the center of the first 3"×3" testing area. Twist the disk through two full revolutions in ⅛ revolution increments. Carefully remove the weight (up and away from the drawdown), and remove the abrading disk from the bottom of the weight. (Only change the double sided tape when a disk will no longer firmly adhere to the bottom of the weight.)
d. Perform steps 3a, 3b, & 3c for all subsequent Leneta card drawdowns.
3. Color Measurement
a. Turn on the Microflash by flipping the toggle switch located on the back panel.
b. Press the 'Menu' key on the front of the microflash until the word "Set-up" appears.
c. Click the button directly below the word "set-up" to select the set-up menu.
d. Use the arrow keys to pick the calibration program.
e. Set the 'hand-held head' to Specular Included. (Using the toggles on the head, confirm that "white" (vs black) is showing through port.)
f. The calibration program prompts you to place the white tile under the microflash head and press the trigger.
g. The prompt that instructs you to measure the Black Trap. Place the black trap under the head and squeeze the trigger.
h. The calibration is now complete.
i. Using the toggles on the back of the Microflash's hand-held head, set the Specular to "Excluded". (Confirm that "black" is showing through the port.)
j. Select 'Illuminant' from the Main Menu. Use the D65/10 setting.
k. Select Display from the main menu. Select CIE LCH Data and choose add.
l. To take measurements, press the large Menu Key on the front of the Microflash.
m. Select 'STD' from the menu. Select 'Temporary Standard'. Place the Microflash over an unused "WypAll" disc over the white section of an unused Leneta card and take a reading by squeezing the trigger. This measurement is now set as the standard.
n. Place a "WypAll" disc that has abraded a product film over the white section of an unused Leneta card then place the Microflash over the disk and take a reading by squeezing the trigger.
o. Record the Delta L value (DL). Take 2 additional measurements of the sample, measuring a different area of the disk each time. The reported result for the test is the absolute value of the average of the 3 measurements.

Example 1

A semi-permanent mascara composition according to the present invention is made having the composition of Table 1A according to the method given directly below Table 1A. The exemplary compositions are identified as prototypes 006, 017, 036 and 089 in Table 1A.

TABLE 1A

Inventive Mascara Compositions

| Phase | Material | Supplier/Trade Name | Function | 006 Wt % | 017 Wt % | 036 Wt % | 089 Wt % |
|---|---|---|---|---|---|---|---|
| A | Tall Oil Glycerides | Arizona Chemical Sylvagum RE 85K | Film Former | 12.5 | 8.5 | 12.5 | 12.5 |
| A | Pentaerythrityl Hydrogenated Rosinate | Eastman Foral 105-E | Film Former | 12.5 | 8.5 | 12.5 | 12.5 |
| A | 1,2 Hexanediol and Caprylyl Glycol | Symrise Symdiol 68 | Preservative | 1 | 1 | 1 | 1 |
| A | Isododecane | Presperse Permthyl 99A | Volatile Solvent | 45.88 | 53.88 | 50.50 | 45.88 |
| B | Disteardimonium Hectorite | Elementis Bentone 38V CG | Structurant | 14 | 14 | 14 | 14 |
| C | Propylene Carbonate | Huntsman Jeffsol | Polar Activator | 4.62 | 4.62 | — | 4.62 |
| D | Black Iron Oxide (Jet Milled) | Sensient Unipure Black LC 989 EM | Colorant | 9.5 | 9.5 | 9.5 | — |
| D | Triethoxycaprylsilane coated Black Iron Oxide (Jet Milled) | Sensient Unipure Black LC 989 EM AS | Colorant | — | — | — | 9.5 |
| | TOTAL | | | 100.000 | 100.000 | 100.000 | 100.00 |

Phase A ingredients are melted and mixed together with low shear mixing. Phase B is gradually added to the Phase A and then dispersed with high shear mixing. Phase C is then added and mixed in with high shear mixing. Phase D is then added and dispersed with high shear mixing. The batch is cooled to ambient conditions.

To demonstrate the superior performance of the new semi-permanent formula technology, the semi-permanent mascara composition of Table 1A was compared to several benchmarks selected from currently marketed mascara products. Benchmark products were selected for water resistant, waterproof, long wear, and semi-permanent stain product types. The comparative products are listed in Table 1B.

TABLE 1B

Comparative Mascara Products (benchmarks)

| Manufacturer | Mascara Name | Mascara Type |
| --- | --- | --- |
| Cover Girl ® | Lash Exact Waterproof ® | Waterproof |
| Cover Girl ® | Lash Exact ® | Water resistant |
| Maybelline ® | Define-A-Lash Waterproof ® | Waterproof |
| Maybelline ® | Define-A-Lash ® | Water resistant |
| Maybelline ® | XXL Pro 24HR Bold ® | Water resistant/Waterproof |
| Tarte ® | 4 day Stay Lash Stain ® | Semi-permanent Lash Stain |

The Cover Girl Lash Exact®, Cover Girl Lash Exact Waterproof®, Maybelline Define-A-Lash®, and Maybelline Define-A-Lash Waterproof® were selected because they have formulations that are typical of commercially available water resistant and waterproof mascara products. The Maybelline XXL Pro 24 HR Bold® product was selected because it has the longest wear duration claim among commercially available long wear mascara products. The Tarte 4 Day Stay Lash Stain® product was selected because it has the longest wear duration claim among commercially available semi-permanent lash stain products.

The products were evaluated in three ways. Scanning electron microscopy was done to characterize the film morphology. Technical testing was performed to evaluate abrasion resistance. Finally, a multi-day consumer usage test was done to assess wear performance in actual usage.

Scanning Electron Microscopy

Scanning electron microscopy (SEM) was used to compare the morphologies of mascara films applied to false lashes. A set of Ardell 109 False Eyelashes® were trimmed to a length of 0.9524 cm and affixed to a metal bar. Five strokes of mascara were applied to a false eyelash sample using an Automated Mascara Applicator device. The samples were allowed to dry completely. Individual lashes were removed from the metal bar and adhered to an SEM sample stub with carbon tape. The edges of the lashes were secured with silver paint. Samples were frozen in liquid nitrogen and transferred to the Alto 2500 sample chamber to defrost at −95 C for 10 minutes. Samples were lightly coated with platinum before observation. Samples were observed using a Hitachi S4700 field emission SEM equipped with a Gatan Alto 2500 cryo stage and representative images were collected at −105 C in the cryo-SEM under the following conditions: kV=3 kV, $I_e$=10 µA, Mode=ultra high resolution, Detector=Mixed, Working Distance=~15 mm.

Cryo-SEM was performed on films of the new semi-permanent formula technology, Cover Girl Lash Exact Waterproof Very Black®, Cover Girl Lash Exact Very Black®, Maybelline XXL Pro 24 HR Bold Mascara Very Black®, and Tarte 4 day Stay Lash Stain®. The SEM shows that the hypothesized film structure is correct. The SEM clearly shows that the new semi-permanent formula technology produces a continuous film that smoothly coats the lash surface. Even at increased magnification (5000×) the surface is smooth with bits of pigment (appearing as white dots) showing through. The films produced by the Cover Girl Lash Exact Waterproof Very Black®, Cover Girl Lash Exact Very Black®, Maybelline XXL Pro 24 HR Bold Mascara Very Black®, and Tarte 4 day Stay Lash Stain® do not have this smooth, continuous morphology. The SEM images are shown in FIGS. 3-6.

Rub Test

Figure 7:
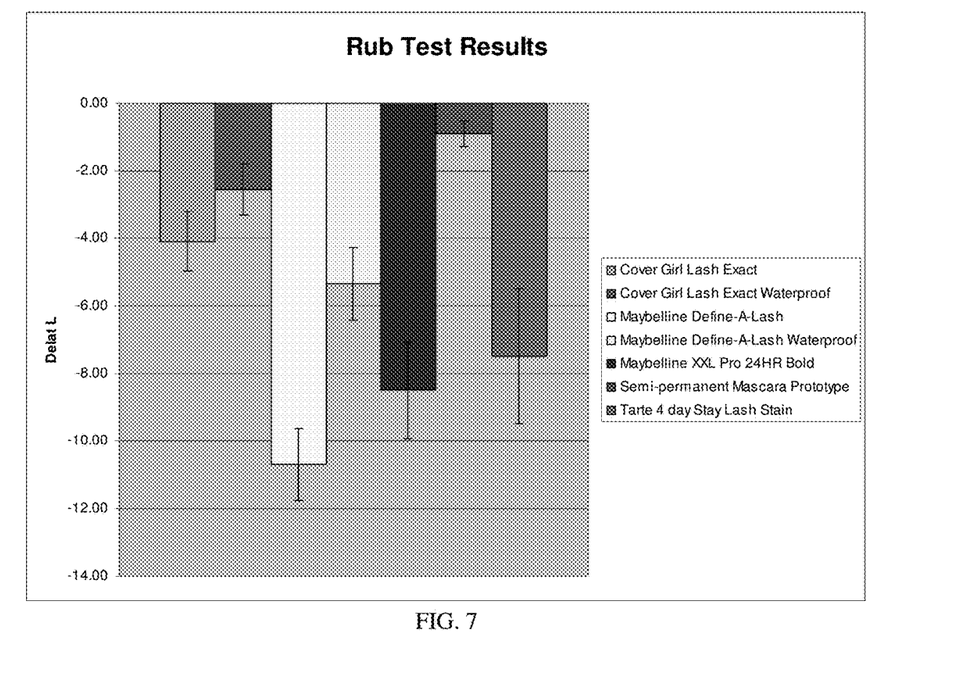
FIG. 7 shows rub test results showing the new semi-permanent formula technology has superior abrasion resistance to current mascara technologies.

The Rub Test method (detailed in the Test Methods section above) was followed. The Rub Test demonstrated that the new semi-permanent formula technology has greater abrasion resistance than any of the water resistant, waterproof, long wear, and semi-permanent benchmarks. The data is shown in FIG. 7.

| | Avg ΔL |
| --- | --- |
| Inventive Mascara Compositions | |
| Prototype 006 | 0.20 |
| Prototype 089 | 0.67 |
| Prototype 017 | 0.88 |
| Benchmark Compositions | |
| Cover Girl Lash Exact Water Proof Very Black ® | 2.54 |
| Cover Girl Lash Exact Very Black ® | 4.09 |
| Maybelline Define-A-Lash Waterproof Mascara Very Black ® | 5.34 |
| Tarte 4 day Stay Lash Stain ® | 7.48 |
| Maybelline XXL Pro 24HR Bold Mascara Very Black ® | 8.49 |
| Maybelline Define-A-Lash Mascara Very Black ® | 10.70 |

Consumer Test

A study was conducted to assess the visual wear advantages of the multi-day mascara prototype described here versus a subset of the comparative mascaras listed in Table 1B. Prior to the application of each test product, lashes were treated the evening before with COVERGIRL Clean Eyes and Lips Make-Up Remover® and rinsed with water to ensure that lashes were mascara residue free at time of test product application the following morning. Further, panelists were given specific facial cleanser and facial moisturizer products to use daily to ensure consistent skin treatment and consistent cleansing and skin care exposure between panelists and test products. This study was a multi-product test with images (see FIG. 8) taken at baseline (bare lashes), immediately after application, 8 hours (end of day 1), 24 hours (beginning of day 2), 32 hours (end of day 2), 48 hours (beginning of day 3) and 56 hours (end of day 3). If the product continued to wear beyond day 3, additional images were taken at extended time points until the product was judged to no longer provide the desirable appearance benefits (as determined by the test moderator). Prior to the end of day 3, if product is no longer observed, no additional images were taken. Each panelist rotated through the 5 test products randomly. Panelists were instructed to apply the product until they got to their desired end look. Images were captured on a Fujifilm FinePixS1Pro Camera® using an external flash with a focal length of 105 mm.

Figure 8:
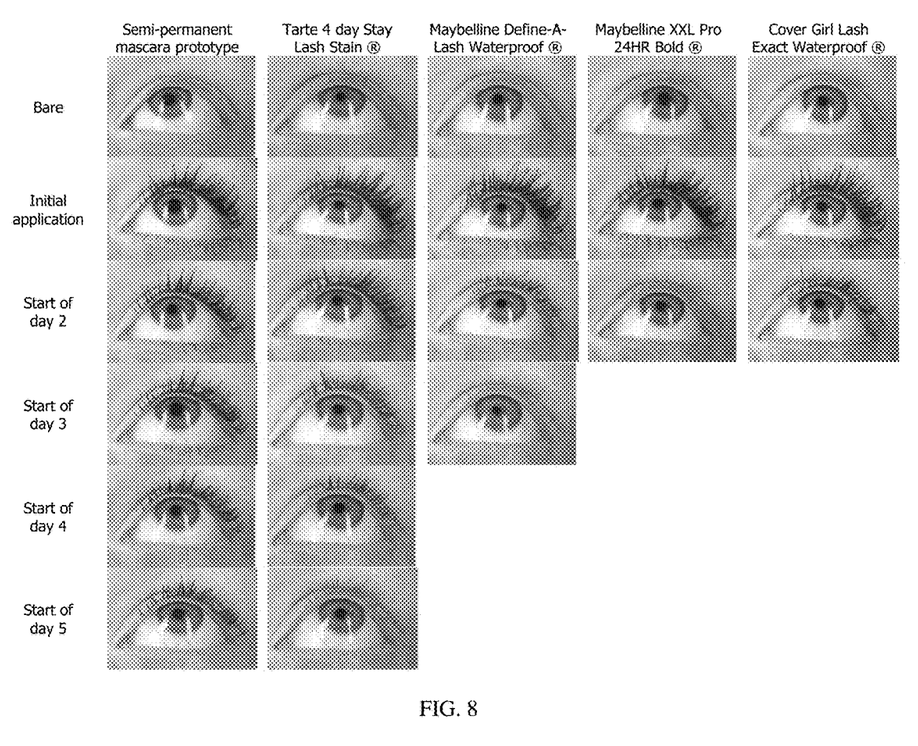
FIG. 8 depicts consumer images showing the new semi-permanent formula technology has superior wear and longevity of mascara beauty benefits over multiple days versus comparative benchmarks.

The consumer test demonstrated that the new semi-permanent formula technology provides true mascara beauty benefits over multiple days better than the comparative benchmarks. FIG. 8 demonstrates the difference in longevity of overall wear and mascara beauty benefits versus the comparative mascara set. The model chosen for the figure has very fair bare eyelashes, providing an excellent basis for product comparison. Although the lash stain product provided some darkness for multiple days, neither the lash length nor volume conferred by the product nor the longevity of product wear was at the level of the new semi-permanent formula technology. All of the waterproof formulas tested provided an initial beauty benefit of long, dark, full lashes versus the bare lash image, but the comparative waterproof mascaras do not provide an acceptable beauty look at the start of day 2 after normal wear, washing and sleeping. Further, none of these products lasted beyond day 2. The consumer images of FIG. 8 shows that the new semi-permanent formula technology has superior wear and longevity of mascara beauty benefits over multiple days versus comparative benchmarks.

Example 2

Four inventive semi-permanent mascara compositions were prepared as detailed in Table 1A above, in Example 1. Three comparative mascara compositions disclosed in Table 2A were prepared as disclosed in JP 2009-114099 (by Kose).

TABLE 2A

Comparative Mascara Compositions

| No. | Component | Trade Name | Ex 1 % W | Ex 2 % W | Ex 9 % W |
|---|---|---|---|---|---|
| 1 | Hydrogenated ester gum | Pine crystal KE-311 | 8 | 15 | 8 |
| 2 | Hydrogenated Pentaerythrityl Rosinate | Ester gum HP | 8 | 10 | 8 |
| 3 | Carnauba Wax | | 3 | 3 | 3 |
| 4 | Beeswax | | 5 | 5 | 5 |
| 5 | Dextrin fatty acid ester | Rheopearl TL | 3 | 3 | — |
| 6 | Organic modified bentonite | | 2 | 2 | 2 |
| 7 | Silicone-treated black iron oxide | 5% dimethicone treatment | 8 | 8 | 8 |
| 8 | Talc | | 5 | 5 | 5 |
| 9 | Sericite | | 2 | 2 | 2 |
| 10 | Silicic anhydride | Aerosil 200 | 2 | 2 | 2 |
| 11 | Light liquid isoparaffin | IP Sorbent 1620MU | qs | qs | qs |
| | TOTAL | | 100 | 100 | 100 |

Examples 1, 2, and 9 of JP 2009-114099 were prepared as follows:
A. Components 1-3 were heated to 110° C. and mixed to homogeneity.
B. Components 4-11 were added to A and mixed to homogeneity.
C. B was filled in containers and oil-based mascaras were obtained.

The Rub Test method was followed to evaluate the abrasion resistance of each of the compositions. As shown in Table 2B, the Rub Test demonstrated that the inventive semi-permanent mascara compositions have greater abrasion resistance than the Kose compositions.

TABLE 2B

Rub Test Results

| | Avg ΔL |
|---|---|
| Inventive Mascara Compositions | |
| Prototype 006 | 0.20 |
| Prototype 017 | 0.88 |
| Prototype 036 | 1.65 |
| Prototype 089 | 0.67 |
| Comparative Compositions | |
| JP 2009-114099 Mascara Example # 1 | 3.56 |
| JP 2009-114099 Mascara Example # 2 | 4.70 |
| JP 2009-114099 Mascara Example # 9 | 4.27 |

Example 3

Table 3 lists the composition for an exemplary top coat for use over a mascara composition.

TABLE 3

Top Coat Composition

| Raw Material Description | Supplier/ Trade Name | Function | % Wt/Wt |
|---|---|---|---|
| Isododecane | Presperse Permthyl 99A | Volatile Solvent | 49.995% |
| Trimethylsiloxysilicate | Momentive MQ Resin | Film Former | 38.025% |
| Dimethicone | Momentive SE-30 Gum | Film Former | 10.980% |
| 1,2 Hexanediol, Caprylyl Glycol | Symrise Symdiol 68 | Preservative | 1.000% |
| | | TOTAL | 100.000% |

Example 4

Table 4 shows an exemplary semi-permanent mascara composition according to the present invention. The exemplary semi-permanent mascara composition was prepared according to the method immediately following Table 4.

TABLE 4

Semi-Permanent Mascara Composition

| Phase | Material | Wt % |
|---|---|---|
| A | Isododecane | 45.5 |
| A | 1,2 Hexandiol and Caprylyl Glycol | 1 |
| A | Benzyl Alcohol | 0.65 |
| B | Tall Oil Glycerides | 13.5 |
| B | Pentaerythrityl Hydrogenated Rosinate | 13.5 |
| C | Black Iron Oxide (Jet Milled) | 10 |
| D | Disteardimonium Hectorite | QS |

Phase A ingredients are melted and mixed together with low shear mixing. Phase B is gradually added to the Phase A and then dispersed with high shear mixing. Phase C is then added and dispersed with high shear mixing. Phase D is added and the batch is cooled to ambient conditions.

Consumer demand for semi-permanent mascara is growing. Current long-wear mascara products do not provide multi-day beauty. It has been found that by using rosinate film-forming polymers, which have a superior combination of stretch resistance, abrasion resistance, and water and surfactant resistance, and by balancing the levels of the polymers and other non-volatile ingredients such that the product forms a continuous polymer film, a mascara formula can provide a multi-day beauty benefit. Cryo-SEM of the mascara film on false lashes shows that the new semi-permanent formula technology produces a continuous film with a smooth surface. This film morphology is different than that of other current mascara technologies, which have films that are broken up by pigments, wax crystals, and other thickening agents. The technical testing demonstrated that the new semi-permanent formula technology has good film flexibility and water and surfactant resistance. However, current semi-permanent technologies and waterproof mascaras also have good water and surfactant resistance and current waterproof mascaras have good film flexibility. The new semi-permanent mascara's abrasion resistance is what differentiates it from current mascara products. The rub test indicates that it had superior performance to current water resistant, waterproof, long wear, and semi-permanent products. The multi-day consumer usage study showed that only the new semi-permanent formula technology provided a multi-day beauty benefit.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A semi-permanent mascara composition, which is an anhydrous dispersion that has low solubility to soap and water, the mascara composition comprising:
    a. from about 15% to about 35%, by weight, of a film former comprising tall oil glyceride and pentaerythrityl rosinate;
    b. from about 0.1% to about 14%, by weight, of a colorant;
    c. less than about 3%, by weight, of a wax; and
    d. a volatile carrier.

2. The mascara composition of claim 1, wherein the film former consists of the tall oil glyceride and the pentaerythrityl rosinate.

3. The mascara composition of claim 1, wherein the pentaerythrityl rosinate is pentaerythrityl hydrogenated rosinate.

4. The mascara composition of claim 3, wherein the film former consists of the tall oil glyceride and the pentaerythrityl hydrogenated rosinate.

5. The mascara composition of claim 1, further comprising glyceryl rosinate.

6. The mascara composition of claim 5, wherein the film former consists of the tall oil glyceride, the pentaerythrityl rosinate, and the glyceryl rosinate.

7. The mascara composition of claim 5, wherein the glyceryl rosinate is glyceryl hydrogenated rosinate.

8. The mascara composition of claim 1, comprising from about 17% to about 35%, by weight, of the film former.

9. The mascara composition of claim 1, comprising from about 20% to about 35%, by weight, of the film former.

10. The mascara composition of claim 1, wherein a ratio of the film former to the volatile carrier is such that the applied mascara composition dries to form a dried film, wherein from about 30% to about 70%, by weight, of the dried film is the film former.

11. The mascara composition of claim 1, wherein a ratio of the film former to the volatile carrier is such that the applied mascara composition dries to form a dried film, wherein from about 40% to about 60%, by weight, of the dried film is the film former.

12. The mascara composition of claim 1, wherein a ratio of the film former to the volatile carrier is such that the applied mascara composition dries to form a dried film, wherein about 50%, by weight, of the dried film is the film former.

13. The mascara composition of claim 1, which comprises less than about 1% by weight of the wax.

14. The mascara composition of claim 1, which comprises less than about 0.1% by weight of the wax.

15. The mascara composition of claim 1, which is substantially free of wax.

16. The mascara composition of claim 1, further comprising a thickener, which includes disteardimonium hectorite particles.

17. The mascara composition of claim 16, wherein the thickener consists of the disteardimonium hectorite particles.

18. The mascara composition of claim 16, wherein the disteardimonium hectorite particles have a diameter that is less than 10 microns.

19. The mascara composition of claim 16, wherein the disteardimonium hectorite particles have a diameter that is less than a thickness of a dried film that is formed when the applied mascara composition dries.

20. The mascara composition of claim 16, wherein the disteardimonium hectorite particles comprise from about 1% to about 25%, by weight, of the mascara composition.

21. The mascara composition of claim 16, wherein the disteardimonium hectorite particles comprise from about 2% to about 20%, by weight, of the mascara composition.

22. The mascara composition of claim 16, wherein the disteardimonium hectorite particles comprise from about 3% to about 15%, by weight, of the mascara composition.

23. The mascara composition of claim 1, wherein the volatile carrier comprises from about 10% to about 85%, by weight, of the mascara composition.

24. The mascara composition of claim 1, wherein the volatile carrier comprises from about 15% to about 80%, by weight, of the mascara composition.

25. The mascara composition of claim 1, wherein the volatile carrier comprises from about 20% to about 70%, by weight, of the mascara composition.

26. The mascara composition of claim 1, wherein the volatile carrier comprises one or more volatile hydrocarbons.

27. The mascara composition of claim 1, wherein the volatile carrier consists of one or more volatile hydrocarbons.

28. The mascara composition of claim 1, wherein the volatile carrier comprises one or more volatile silicones.

29. The mascara composition of claim 1, wherein the volatile carrier consists of one or more volatile silicones.

30. The mascara composition of claim 1, wherein the volatile carrier comprises isoparaffin.

31. The mascara composition of claim 1, wherein the volatile carrier consists of isoparaffin.

32. The mascara composition of claim 1, wherein the volatile carrier comprises isododecane.

33. The mascara composition of claim 1, wherein the volatile carrier consists of isododecane.

34. The mascara composition of claim 1, wherein the mascara composition is a first layer, and further comprising a second layer configured to be applied on top of the first layer.

35. The mascara composition of claim 34, wherein the second layer is configured to mitigate a tackiness of the first layer.

36. The mascara composition of claim 34, wherein the second layer is configured to extend a wearability of the first layer.

37. The mascara composition of claim 34, wherein the second layer is anhydrous.

38. The mascara composition of claim 34, wherein the second layer includes a film forming polymer.

39. The mascara composition of claim 34, wherein the second layer comprises less than about 3% by weight of colorant.

40. The mascara composition of claim 34, wherein the second layer comprises less than about 1% by weight of colorant.

41. The mascara composition of claim 34, wherein the second layer comprises less than about 0.1% by weight of colorant.

42. The mascara composition of claim 34, wherein the second layer has no colorant.

43. The mascara composition of claim 34, wherein the second layer is clear.

44. The mascara composition of claim 38, wherein the film forming polymer is an organosiloxane resin.

45. The mascara composition of claim 44, wherein the organosiloxane resin comprises from about 10% to about 95%, by weight, of the second layer.

46. The mascara composition of claim 44, wherein the organosiloxane resin comprises from about 55% to about 80%, by weight, of the second layer.

47. The mascara composition of claim 44, wherein the organosiloxane resin comprises from about 60% to about 70%, by weight, of the second layer.

48. The mascara composition of claim 38, wherein the film forming polymer includes trimethylsiloxysilicate.

49. The mascara composition of claim 48, wherein the film forming polymer includes dimethicone.

50. The mascara composition of claim 34, wherein the second layer includes a volatile carrier.

51. The mascara composition of claim 34, wherein the second layer includes a volatile carrier, which is isododecane.

* * * * *